United States Patent [19]
Rosen et al.

[11] Patent Number: 5,295,955
[45] Date of Patent: Mar. 22, 1994

[54] METHOD AND APPARATUS FOR MICROWAVE AIDED LIPOSUCTION

[75] Inventors: Daniella Rosen; Arye Rosen, both of Cherry Hill Township, Camden County, N.J.

[73] Assignee: AMT, Inc., Cherry Hill, N.J.

[21] Appl. No.: 837,339

[22] Filed: Feb. 14, 1992

[51] Int. Cl.$^5$ .............................................. A61B 17/20
[52] U.S. Cl. ........................................ 604/22; 604/49; 607/101; 607/116; 606/33
[58] Field of Search ............... 128/786, 804, 24 AA, 128/898; 604/22, 49, 902, 27; 606/169-171, 32-34; 607/101, 116

[56] References Cited

U.S. PATENT DOCUMENTS

| | | | |
|---|---|---|---|
| 3,823,717 | 7/1974 | Pohlman et al. | 604/22 |
| 4,632,127 | 12/1986 | Sterzer | 128/804 |
| 4,643,186 | 2/1987 | Rosen et al. | 128/804 |
| 4,692,139 | 9/1987 | Stiles | 604/22 |
| 4,735,604 | 4/1988 | Watmough et al. | 604/22 |
| 4,808,153 | 2/1989 | Parisi | 604/22 |
| 4,813,429 | 3/1989 | Eshel et al. | 128/736 |
| 4,815,462 | 3/1989 | Clark | 604/902 |
| 4,823,812 | 4/1989 | Eshel et al. | 128/804 |
| 4,886,491 | 12/1989 | Parisi et al. | 604/902 |
| 4,931,047 | 6/1990 | Broadwin et al. | 604/22 |
| 4,936,281 | 6/1990 | Stasz | 604/22 |
| 4,967,765 | 11/1990 | Turner et al. | 128/804 |
| 5,007,437 | 4/1991 | Sterzer | 128/804 |
| 5,015,227 | 5/1991 | Broadwin et al. | 604/22 |
| 5,057,106 | 10/1991 | Kasevich et al. | 128/804 |
| 5,058,590 | 10/1991 | Wurster | 604/22 |
| 5,123,903 | 6/1992 | Quaid et al. | 604/22 |
| 5,143,063 | 9/1992 | Fellner | 128/897 |
| 5,154,165 | 10/1992 | Elliott et al. | 604/20 |
| 5,181,907 | 1/1993 | Becker | 604/22 |
| 5,190,518 | 3/1993 | Takasu | 604/902 |

*Primary Examiner*—C. Fred Rosenbaum
*Assistant Examiner*—Michael Rafa
*Attorney, Agent, or Firm*—William H. Meise

[57] ABSTRACT

Fatty tissue involved in a liposuction procedure is treated with microwave energy (also known as RF). In a particular embodiment of the invention, the microwave energy is applied by means of a catheter including a suction lumen, an electromagnetic transmission line, and an antenna coupled to the distal end of the transmission line. A microwave generator coupled to the distal end of the transmission line causes radiation from the antenna into the fatty tissue adjacent to the distal suction port of the suction lumen, which tissue is thereby heated and softened. The softened fatty tissue is more readily detached from the adjacent tissue than in the absence of heat, and less mechanical force is required for removal. In another embodiment of the invention, the transmission line is formed so that the electromagnetic field extends into the suction lumen, so that the fatty tissue being removed therethrough continues to be heated. Saline solution or other liquid with polar molecules is injected into the region being treated to provide improved coupling of energy between the electromagnetic radiation and the fatty tissue. Microwave radiation may be applied to the region being treated by means of an external radiator. The heating effect of the radiation not only softens the tissue for ready removal, but also tends to sterilize the region for reducing infection.

11 Claims, 3 Drawing Sheets

METHOD AND APPARATUS FOR MICROWAVE AIDED LIPOSUCTION

BACKGROUND OF THE INVENTION

This invention relates to medical procedures generally, and more specifically to microwave (a subset of radio-frequency) electromagnetic radiation used for aiding in liposuction.

Liposuction is a procedure by which fatty tissue is removed from portions of the body by percutaneous insertion of a tube catheter into the fatty tissue, and by application of suction to the proximal end of the tube. The distal end of the catheter is moved about through the fatty tissue, to mechanically loosen its attachment to adjacent tissue. Suction applied to the proximal end of the tube draws the loosened fatty tissue through the tube to a discharge container.

Liposuction treatment requires vigorous manipulation of the suction catheter to dislodge the fatty tissue, and gives rise to the possibility of undesired injury to other tissues of the patient. Also, the drawing of matter through the catheter tube from the interior of the body inevitably results in drawing of some microbial matter into the body as pressures equalize, thereby giving rise to the possibility of infection. An improved liposuction technique is desired.

SUMMARY OF THE INVENTION

In accordance with the invention, the fatty tissue involved in a liposuction procedure is treated with microwave or other RF energy during the procedure. In a particular embodiment of the invention, the electrical energy is applied by means of a catheter including a suction lumen or tube, an electromagnetic transmission line, and an antenna, which is coupled to the distal end of the transmission line. At frequencies below those of microwaves, a means for coupling energy, such as a simple wire, may be used instead of an antenna. A generator coupled to the distal end of the transmission line causes transmission of RF into the fatty tissue adjacent to the distal suction port of the suction lumen. The tissue is thereby heated and softened. The softened fatty tissue is more readily detached from the adjacent tissue than in the absence of heat, and less mechanical force is required for removal. In another embodiment of the invention, the transmission line is formed so that the electromagnetic field extends into the suction lumen, so that the fatty tissue being removed therethrough continues to be heated, and cannot cool and become more viscous, which might possibly cause the suction lumen to clog. In yet another embodiment of the inventive method, water, saline solution or other liquid with polar molecules is injected into the region being treated to provide improved coupling of energy between the electromagnetic field and the fatty tissue. The rate of influx of the water may be adjusted so that a small positive pressure is maintained within the region being treated, so that microbial influx is reduced, increased pressure differential tending to move material through the suction lumen. In yet another embodiment, RF/microwave energy is applied to the region being treated by means of an external radiator. The heating effect of the radiation not only softens the tissue for ready removal, but also tends to sterilize the region for reducing the possibility of infection.

DESCRIPTION OF THE INVENTION

Figure 1A:
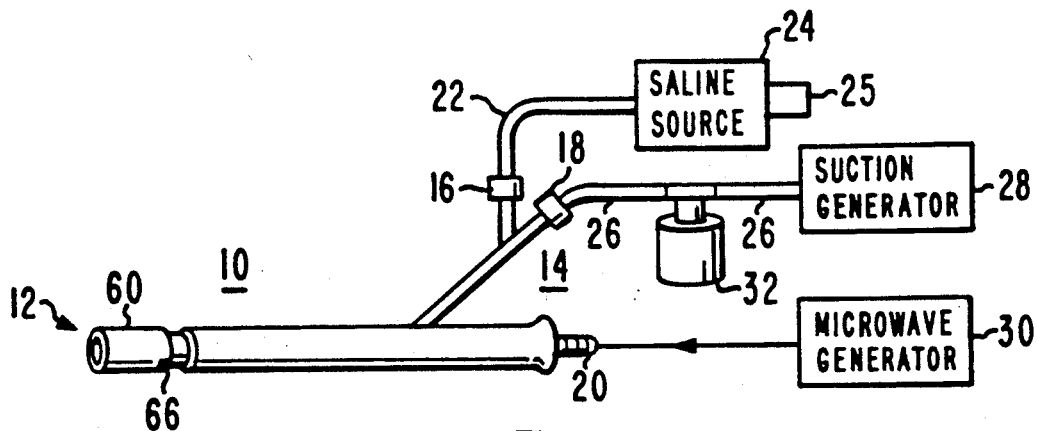
FIG. 1a is a pictorial diagram of a catheter system according to the invention, illustrating a suction lumen, a polar liquid injection lumen, a transmission line and a coupling arrangement, which at high RF frequencies is an antenna.

FIG. 1a is a pictorial representation of a catheter system useful in performing liposuction in accordance with the invention. In FIG. 1a, an elongated catheter end designated generally as 10 includes a distal end 12, and a proximal end designated generally as 14. Proximal end 14 of catheter 10 includes a variety of terminations 16, 18 and 20. Proximal termination 16 includes a liquid port coupled by a tube 22 to a source 24 of a polar liquid such as water. An aqueous solution such as saline, preferably sterile, may also be used. A polar liquid is preferred because nonpolar liquids are not effectively heated by electromagnetic energy. Termination 18 is a liquid port, which is coupled by a tube 26 to a source of suction 28. Termination 20 is coupled to a source of microwave energy. The term microwave is used in a generic sense to include those forms of energy known as RF, and also millimeter-wave.

Figure 1B:
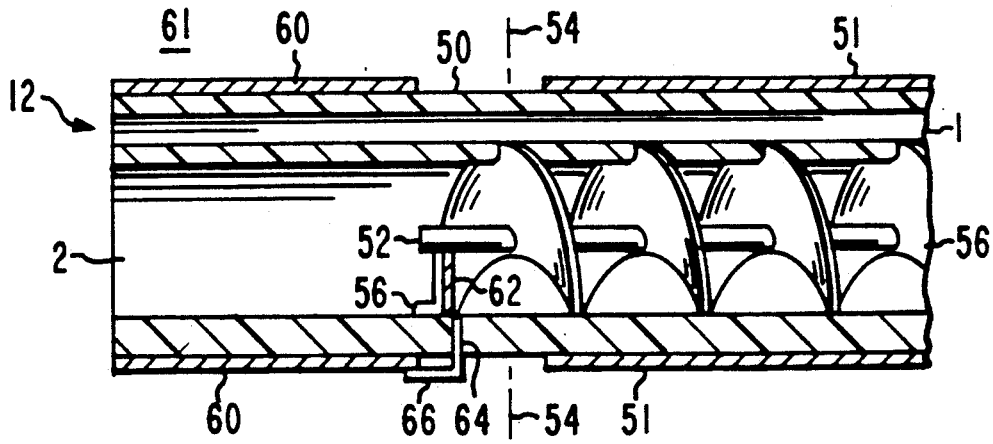
FIG. 1b is a cross-section of the distal end of the catheter of FIG. 1a, FIG. 1c is a phantom view of a center conductor support structure which may be used in a transmission line according to an embodiment of the invention.

Liquid ports 16 and 18 extend independently, through first and second lumens, from the proximal end 14 of catheter 10 to its distal end 12. Similarly, microwave termination 20 connects to a transmission line which extends distally. FIG. 1b is a cross-section of catheter 10 near its distal end. As illustrated in FIG. 1b, catheter 10 includes a dielectric or nonconductive body 50, shaped to define a first relatively small liquid lumen 1, which communicates with liquid port 16 of FIG. 1a. Body 50 as illustrated in FIG. 1b also defines a larger lumen 2 which extends from distal end 12 of catheter 10 to liquid port 18 illustrated in FIG. 1a.

Figure 1C:
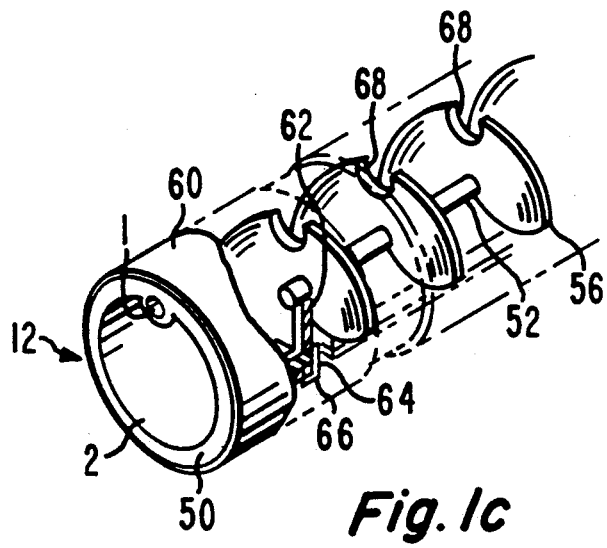
FIG. 1d illustrates another type of center conductor support.

The outer surface of catheter body 50 in FIG. 1b is covered by a first electrically conductive layer 51, which extends proximally to port 20, thereby forming the outer conductor of a coaxial transmission line. A coaxial inner conductor 52 extends through the center of lumen 2 of catheter 10, and is held in place by a continuous helical dielectric spacer illustrated as 56. Both outer conductor 51 and inner conductor 52 extend distally to locations near a transverse plane 54, which represents the distal end of the transmission line. The outer surface of catheter body 50 includes a second electrically conductive layer 60, which extends from distal end 12 toward plane 54. Layer 60 is spaced away from, and electrically isolated from, layer 51. Layer 60 is in electrical communication with the distal end of center conductor 52, by way of a layer of conductor 62 extending from center conductor 52 over the surface of helical spacer 56 to a rivet or conductive via 64, and a conductive tab 66 extending from rivet 64 to layer 60. In effect, conductive layer 60 is a monopole antenna, designated generally as 61, acting against (having field lines extending to) the outer surface of layer 51. FIG. 1c is a perspective or isometric view, partially in phantom, illustrating the connection path between center conductor 52 and layer 60, and also illustrating the helical form of support 56. Notches 68 associated with each turn of helical support 56 are for clearing that portion of the body 50 which contains lumen 1.

Antenna 61 formed by layer 60 in conjunction with the outer surface of outer conductor layer 51 couples electromagnetic energy propagated from microwave generator 30 to the space around the distal end 12 of the catheter. Those skilled in the art will know how to adjust the shape and or dimensions of antenna 61 to suit the frequency of operation. For example, portion 60 could be extended in an axial direction for lower frequencies, and at yet lower frequencies could be coiled into a helical shape. Lumen 1 allows aqueous saline solution flowing from source 24 to exit from the distal end of the catheter.

In operation, the distal end 12 of the catheter is inserted subcutaneously into the body of a patient at the region to be treated by liposuction, and RF/microwave energy is applied from generator 30 of FIG. 1a to heat and soften the fatty tissue. Suction is applied from generator 28 of FIG. 1a to large lumen 2, to tend to aspirate or draw away the heated fatty tissue. The catheter is manipulated, tending to dislodge fatty tissue. If the fatty tissue is not sufficiently lossy to adequately absorb energy from the electromagnetic field, saline solution is allowed to enter through lumen 1 to intermix with the fatty tissue, absorb microwave energy, and transfer heat to the fatty tissue. The softened and loosened intermixed material is aspirated through lumen 2 of FIG. 1b and the helical path around support 56 to port 18, and is collected by a closed container 32 of FIG. 1a before it reaches suction generator 28. A temperature of about 45° C. softens fatty tissue, and a temperature of about 50° C. tends to liquify ordinary fat. Temperatures in this range also inhibit microbes.

During the liposuction procedure, the flow rate or flux of saline supplied by source 24 is adjusted with a pressure controller 25, to maintain a seepage from the point of insertion, to thereby reduce ingress of microbes.

Figure 1D:
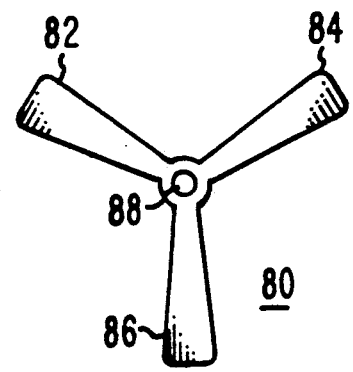

A more conventional support arrangement for center conductor 52 of FIG. 1b includes a plurality of three-lobed structures such as 80 of FIG. 1d. Support 80 includes three legs or lobes 82, 84 and 86, the ends of which are curved to bear against the interior walls of lumen 2 of the structure of FIG. 1b, and which also contains a bore 88 dimensioned to tightly fit the exterior of center conductor 52. As many supports 80 are used as may be required by structural considerations. One support 80 should be placed near plane 54 of FIG. 1b, and that one should be made from electrically conductive material to allow ready connection between the center conductor and distal outer conductive layer 60, while all the other support members 80 should be made from a nonconductive material.

Figures 2A, 2B:
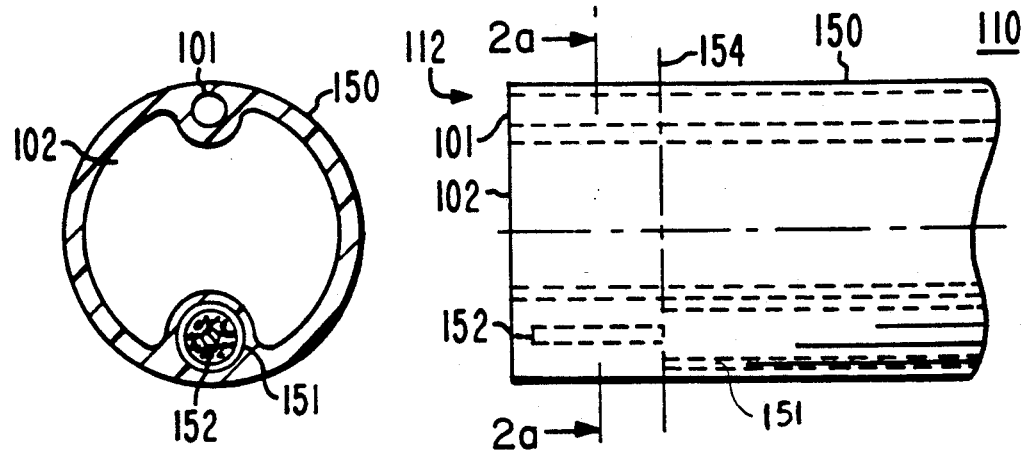
FIG. 2a is a cross-section of another catheter in accordance with the invention, in which a separate coaxial cable extends off-center through a liposuction catheter.
FIG. 2b is a side elevation view thereof.

The arrangement of FIGS. 1a, 1b, 1c, or the 1d variation have the advantage that the electromagnetic fields within the coaxial transmission line made up from outer conductor 51 and inner conductor 52 tend to heat the saline-fat mixture flowing therein, to keep the material soft and thereby prevent "clotting" or coagulation of the material in the lumen, which might cause it to clog. If more energy is desired at the distal end, the loss due to energy transmission through the lossy saline-fat mixture can be avoided by a structure such as that illustrated in FIG. 2a and 2b. In FIG. 2a, elements corresponding to those of FIG. 1b and 1c are designated by like reference numerals in the 100 series. In FIG. 2a, a catheter 110 includes a body 150 of dielectric material which defines a small discharge lumen 101 and a large suction lumen 102. At one side of suction lumen 102, a coaxial transmission line including an outer conductor 151 and a center conductor 152 extends almost to the distal end 112 of the catheter. Outer conductor 151 of the coaxial transmission line ends at a transverse plane 154 of FIG. 2b, and center conductor 152 extends more distally, forming an antenna which is capable of radiating distally propagating energy. While such antennas, in principle, radiate all the energy which they receive from their transmission lines, unavoidable impedance mismatches inevitably result in reflection of some of the incident energy, which therefore cannot be radiated. Center conductor 152 is held concentric with outer conductor 151 in any convenient manner, as by a dielectric foam. The end of the coaxial line and the antenna formed by the extension of center conductor 152 past plane 154 are sealed within the dielectric material of body 150, so liquids cannot enter the coaxial line.

Figure 3:
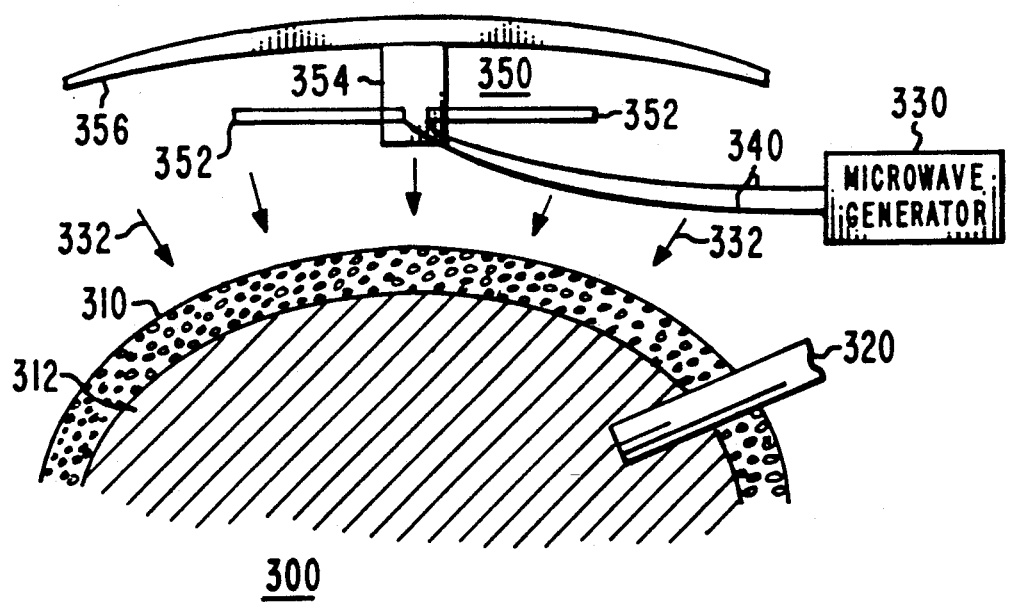
FIG. 3 illustrates use of a suction catheter in combination with a further antenna or other coupling arrangement located external to the body for radiating microwave energy into the region being treated.

FIG. 3 is a representation of another embodiment of the invention for heating the fatty tissue during liposuction. In FIG. 3, a portion 300 of a patient's body includes a dermal or skin region 310 and a fatty tissue portion 312. A tube catheter 320, which may be either of conventional design or of the type described above, is illustrated as having its distal end penetrating beneath the dermal layer and into the underlying fatty tissue 312. A suction source (not illustrated in FIG. 3) is coupled to a suction lumen (not illustrated in FIG. 3) extending through to the distal end of catheter 320. Catheter 320 is manipulated in conventional manner to dislodge fatty tissue for aspiration. At the same time, microwave energy is applied from the exterior of the body, as illustrated by arrows 332. The microwave energy is generated by a generator 330, and applied by a transmission line 340 (in this case illustrated as an open two-wire transmission line) to a directional antenna 350, illustrated as a center-fed dipole 352, which is supported by a dielectric block 354 before a reflector 356. The reflector may be a plane reflector or it may be curved, as required, to achieve the desired directional pattern. Heating by way of an external antenna as depicted in FIG. 3 may be used in conjunction with heating by means of an antenna within catheter 320, as described in conjunction with FIGS. 1a and 2a. In order to avoid uneven heating by formation of "hot spots" due to phase-dependent constructive and destructive interference, separate, non-coherent generators may be used for the interior and exterior heating. This is easily accomplished by using non-synchronized generators operating at different frequencies.

Figure 4:
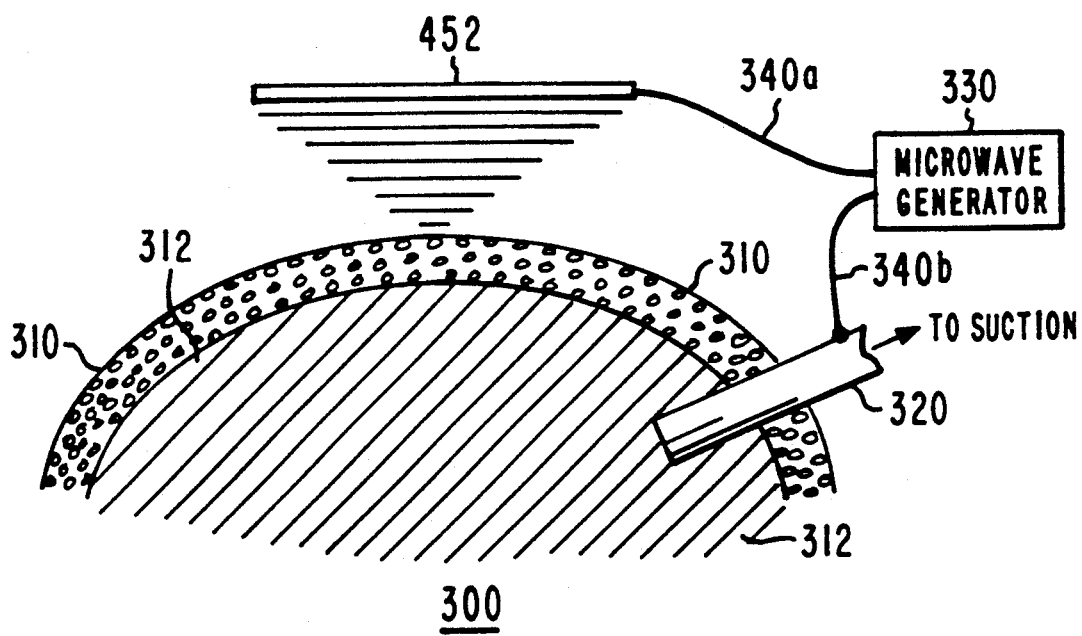
FIG. 4 is similar to FIG. 3, except that the additional electromagnetic energy is applied by an "antenna" which is actually a coupling arrangement, formed partially by the catheter and partially by an external electrode.

FIG. 4 is similar to FIG. 3, and corresponding elements are designated by like reference numerals. In FIG. 4, the exterior of catheter 320 is electrically conductive. Generator 330 generates an alternating voltage between conductors 340a and 340b. Conductor 340a is connected to an electrode 452 positioned outside body 300, and conductor 340b is connected to the conductive exterior of catheter 320. This arrangement generates an electric field between the catheter and the electrode which provides a heating effect as in diathermy. Generally, the form of the connections illustrated in FIG. 4 limits the upper frequencies at which the arrangement may be operated by comparison to the arrangements of FIGS. 1b and 2a.

Other embodiments of the invention will be apparent to those skilled in the art. For example, at RF frequencies near 200 kHz, unshielded two-wire transmission lines may be used to couple to and through the catheter, rather than the coaxial transmission line as described above for use at microwave frequencies. Also, at low RF frequencies near 200 kHz, energy may be coupled into the fatty tissue by a conductor contiguous with (adjacent to and touching, or adjacent to and not touching) the tissue, which is not an antenna in the conventional sense, but which provides coupling by near-field mechanisms other than radiation. Other lumens andor fiber-optic cables may be used with a catheter according to the invention. Many types of conventional antennas may be used, including bifilar and helical antennas. The exterior of the catheter may be covered with an inert plastic coating, if desired. While a rigid catheter is preferred so as to allow the desired manipulation of the distal end, a degree of flexibility may be desirable to prevent injury to the patient.

What is claimed is:

1. A method for liposuction, comprising the steps of:
    inserting a distal end of a hollow tube catheter into a body region of fatty tissue to be treated:
    applying suction to a proximal end of said tube to thereby tend to draw material from said region to be treated; and
    radiating RF/microwave energy to said region to be treated during said step of applying suction, to heat and thereby tend to soften said fatty tissue.

2. A method according to claim 1, further comprising the step of introducing a polar liquid into said region to be treated for aiding in transforming said RF/microwave energy into heat.

3. A method according to claim 2, wherein said step of introducing a polar liquid includes the step of introducing an aqueous liquid.

4. A method according to claim 1, wherein said step of introducing an aqueous liquid comprises the step of generating a flow of said liquid through at least a portion of said region to be treated.

5. A method according to claim 4, wherein said step of generating a flow includes the further steps of;
    generating a flow of said aqueous liquid into said region to be treated; and
    sucking a mixture of said aqueous liquid and said fatty tissue toward said proximal end of said catheter.

6. A method according to claim 1, wherein said step of radiating RF/microwave energy includes the step of radiating electromagnetic energy toward said region to be treated from a directional antenna located outside said body.

7. A method according to claim 1, wherein said step of radiating RF/microwave energy includes the step of introducing said energy into said region to be treated by means of an electromagnetic transmission line.

8. A method according to claim 1, wherein said step of radiating RF/microwave energy includes the step of applying alternating voltage to a pair of electrodes, one of which is within said region to be treated, and the other one of which is outside said body.

9. A method according to claim 1, wherein said step of introducing a hollow tube catheter includes the step of concurrently inserting an electromagnetic antenna and a portion of a transmission line into said region to be treated.

10. A method according to claim 9 wherein said step of radiating RF/microwave energy includes the step of applying microwave energy to a proximal end of said transmission line.

11. A method according to claim 1, wherein said step of radiating RF/microwave energy includes the step of controlling the amount of said energy to tend to maintain the temperature of said fatty tissue in the range of about 45° to 50° C.

* * * * *